United States Patent
Yoo et al.

(10) Patent No.: US 11,896,703 B2
(45) Date of Patent: Feb. 13, 2024

(54) LIQUID LIPID COMPOSITE COMPOSITION FOR IMPROVING HAIR CONDITION

(71) Applicant: AMOREPACIFIC CORPORATION, Seoul (KR)

(72) Inventors: Jae Won Yoo, Yongin-si (KR); Minjin Kim, Yongin-si (KR); Yong Jin Kim, Yongin-si (KR); Jangwon Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 469 days.

(21) Appl. No.: 17/041,300

(22) PCT Filed: Mar. 22, 2019

(86) PCT No.: PCT/KR2019/003368
§ 371 (c)(1),
(2) Date: Sep. 24, 2020

(87) PCT Pub. No.: WO2019/190125
PCT Pub. Date: Oct. 3, 2019

(65) Prior Publication Data
US 2021/0015732 A1    Jan. 21, 2021

(30) Foreign Application Priority Data
Mar. 27, 2018 (KR) ........................ 10-2018-0035249

(51) Int. Cl.
*A61K 8/63* (2006.01)
*A61K 8/42* (2006.01)
*A61K 8/36* (2006.01)
*A61Q 5/12* (2006.01)

(52) U.S. Cl.
CPC ................ *A61K 8/63* (2013.01); *A61K 8/361* (2013.01); *A61K 8/42* (2013.01); *A61Q 5/12* (2013.01)

(58) Field of Classification Search
CPC ... A61Q 5/02; A61Q 5/12; A61Q 5/00; A61K 8/922
See application file for complete search history.

(56) References Cited

U.S. PATENT DOCUMENTS

| 8,313,755 B2 | 11/2012 | Shiroyama et al. |
| 2010/0286102 A1 | 11/2010 | Vielhaber |
| 2015/0231057 A1* | 8/2015 | Pegeon .................. A61P 43/00 424/774 |
| 2017/0216172 A1 | 8/2017 | Carballada et al. |
| 2017/0304180 A1* | 10/2017 | Pang .................. A61K 8/8152 |

FOREIGN PATENT DOCUMENTS

| JP | H10-1423 A | 1/1998 |
| JP | 2001-316217 A | 11/2001 |
| JP | 2005-206524 A | 8/2005 |
| KR | 1998-0008206 A | 4/1998 |
| KR | 10-2005-0026778 A | 3/2005 |
| KR | 10-2006-0057664 A | 5/2006 |
| KR | 10-0713555 B1 | 4/2007 |
| KR | 10-2009-0075821 A | 7/2009 |
| KR | 10-2010-0007169 A | 1/2010 |
| KR | 10-2010-0100202 A | 9/2010 |
| KR | 10-2015-0088602 A | 8/2015 |
| KR | 10-2015-0146011 A | 12/2015 |
| WO | 98/27958 A1 | 7/1998 |
| WO | 03/077861 A2 | 9/2003 |
| WO | 2008/043386 A1 | 4/2008 |
| WO | 2010/005144 A1 | 1/2010 |

OTHER PUBLICATIONS

English translation of KR 20060057664 A obtained from PE2E Search (Year: 2023).*
International Search Report from International Application No. PCT/KR2019/003368, dated Jul. 2, 2019.
Written Opinion from International Application No. PCT/KR2019/003368, dated Jul. 2, 2019.

* cited by examiner

*Primary Examiner* — Robert T. Crow
*Assistant Examiner* — John P Nguyen
(74) *Attorney, Agent, or Firm* — MERCHANT & GOULD P.C.

(57) ABSTRACT

Disclosed in the present specification is a liquid lipid composite composition comprising ceramide, cholesterol, a $C_{10-30}$ unsaturated fatty acid having three or fewer double bonds, and natural oil or wax containing a $C_{10-60}$ fatty acid ester or $C_{10-60}$ fatty acid ester at a weight ratio of 1:0.03-3:2.5-12:0.3-6. The liquid lipid composite composition comprises a high content of ceramide and is present in a liquid state during storage at normal temperature, and thus can be easily applied as a formulation of a hair cosmetic composition. The liquid lipid composite composition, when used to treat hair, has excellent hair condition improving effects, such as improving the softness of the hair, enhancing the elasticity and strength of the hair, and increasing the shininess of the hair.

19 Claims, No Drawings

LIQUID LIPID COMPOSITE COMPOSITION FOR IMPROVING HAIR CONDITION

This application is a National Stage Application of PCT/KR2019/003368, filed Mar. 22, 2019, which claims benefit of Serial No. 10-2018-0035249, filed Mar. 27, 2018 in the Republic of Korea and which applications are incorporated herein by reference. To the extent appropriate, a claim of priority is made to each of the above disclosed applications.

TECHNICAL FIELD

The present disclosure relates to a liquid lipid composite composition including ceramide, cholesterol, an unsaturated fatty acid, and a fatty acid ester, or natural oil or wax including a fatty acid ester as active ingredients.

BACKGROUND ART

Approximately 1-8% of hair includes lipids. It is known that lipids present in hair has a significantly important function in terms of softness, elasticity, strength and shininess of hair and protection of the inner part of hair, and includes ceramide, fatty acids, cholesterol, fatty acid esters, or the like. Lipids present in hair are bound to the surfaces of keratinized cells, hair cuticle and inner root sheath. When hair is formed, the outer part of hair maintains hydrophobic outer surface properties by a covalently bonded lipid layer and cell membrane complex (CMC) lipid composite, and such properties function to protect hair from chemical and physical stimuli from the external environment. Such chemical and physical stimuli may cause damages on hair, including dryness, reduced elasticity, shattering, hair end splitting, dull hair, lusterless appearance, reduced abundance, rough surface and reduced mechanical strength. Therefore, there is a need for developing a hair cosmetic composition for offsetting such negative effects in damaged hair.

Meanwhile, when hair is damaged, lipids present in hair are reduced. Thus, there have been many attempts to improve the condition of hair by using hair lipid ingredients. However, most of such attempts merely use each of hair lipid ingredients and there are not many reports about use of the whole of ceramide, cholesterol, fatty acids and fatty acid esters known as hair lipid ingredients. Particularly, even in the case of use of the whole hair lipid ingredients, it is not easy to introduce a high content of ceramide, which is an important ingredient among the whole hair lipid ingredients, to the formulation of a hair cosmetic composition due to the low solubility of ceramide. In addition, it is preferred that a composite composition simulating hair lipids is present in a liquid state in order to apply the composition smoothly to the formulation of a hair cosmetic composition. However, it is difficult to realize such a liquid composite composition.

Under these circumstances, the present inventors have conducted many studies about a liquid lipid composite composition including a high content of ceramide and present in a stable liquid state, as a lipid composite composition simulating hair lipids. We have found that such a liquid lipid composition can be applied to a hair cosmetic composition effective for improving a hair condition. The present disclosure is based on this finding.

REFERENCES

Patent Document (Patent Document 1) KR 713,555 B

DISCLOSURE

Technical Problem

A technical problem to be solved by the present disclosure is to provide a liquid lipid composite composition which includes ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a specific weight ratio.

Another technical problem to be solved by the present disclosure is to provide a liquid lipid composite composition having an excellent effect of improving a hair condition, and including ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a specific weight ratio.

Technical Solution

In one general aspect, there is provided a liquid lipid composite composition which includes ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a weight ratio of 1:0.3-3:2.5-12:0.3-6.

In another general aspect, there is provided a liquid lipid composite composition for improving a hair condition, which includes ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a weight ratio of 1:0.3-3:2.5-12:0.3-6.

Advantageous Effects

According to the embodiments of the present disclosure, the liquid lipid composite composition, which includes ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a weight ratio of 1:0.3-3:2.5-12:0.3-6, contains a high content of ceramide and is present in a liquid state during storage at room temperature regardless of dilution with non-polar oil, and thus can be easily applied to the formulation of a hair cosmetic composition. In addition, when hair is treated with the liquid lipid composite composition, it is possible to obtain an excellent effect of improving a hair condition, such as effects of enhancing hair softness, increasing hair elasticity and strength, and increasing hair shininess.

BEST MODE

Exemplary embodiments now will be described more fully hereinafter.

In one aspect, there is provided a liquid lipid composite composition which includes ceramide, cholesterol, a $C_{10\text{-}30}$ unsaturated fatty acid having three or fewer double bonds, and a $C_{10\text{-}60}$ fatty acid ester, or natural oil or wax containing a $C_{10\text{-}60}$ fatty acid ester at a weight ratio of 1:0.3-3:2.5-12:0.3-6.

Herein, ceramide is a kind of spingolipid having a structure in which a fatty acid is linked to sphingosine or phytosphingosine, occupies about 40-50% or more of intercellular lipids forming the stratum corneum, and is an essential ingredient for forming the structure of the stratum corneum or realizing the functions of the stratum corneum. Particularly, hair comprises keratinized epithelial cells and ceramide is one of the lipid ingredients forming hair. Ceramide may include natural ceramide, which is naturally occurring ceramide, and pseudoceramide, which is a compound having a lamellar structure of natural ceramide. In addition, ceramide is formed by binding of a sphingosine base, such as dihydrosphingosine, sphingosine, phytosphingosine or 6-hydroxysphingosine, with a fatty acid, such as non-hydroxy fatty acid, α-hydroxy fatty acid, ester-bound ω-hydroxy fatty acid. Since such various sphingosine bases and fatty acids are bound with each other to form ceramides, various types of ceram ides may be present in the stratum corneum. According to the present disclosure, ceramide may be at least one selected from the group consisting of phytosphingosine ceramide, sphingosine ceramide, sphinganine ceramide and psuedoceramide, particularly pseudoceramide, more particularly pseudoceramide represented by the following Chemical Formula 1, even more particularly pseudoceramide represented by the following Chemical Formula 1, wherein R is $C_{11}H_{23}$ or $C_{15}H_{31}$, and most particularly pseudoceramide represented by the following Chemical Formula 2 (Chemical Formula 1, wherein R is $C_{15}H_{31}$), but is not limited thereto.

[Chemical Formula 1]

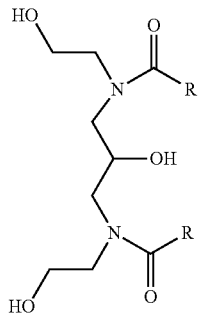

wherein R is a $C_{2-25}$ alkyl.

[Chemical Formula 2]

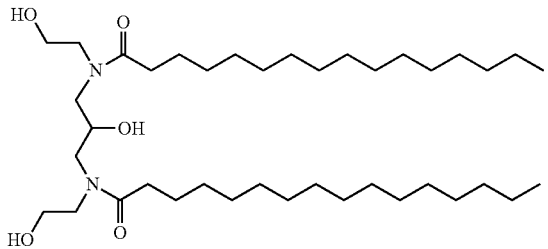

According to the present disclosure, ceramide may be used in an amount of 5-15 wt %, particularly 5 wt % or more, 6 wt % or more, 7 wt % or more, 8 wt % or more, 9 wt % or more, 10 wt % or more, 11 wt % or more, 12 wt % or more, 13 wt % or more, or 14 wt % or more, and 15 wt % or less, 14 wt % or less, 13 wt % or less, 12 wt % or less, 11 wt % or less, 10 wt % or less, 9 wt % or less, 8 wt % or less, 7 wt % or less, or 6 wt % or less, and more particularly 6 wt % or 14 wt %, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester. However, the scope of the present disclosure is not limited thereto.

According to the present disclosure, cholesterol is one of the main lipid ingredients forming hair, and keratinized cells forming hair are bound firmly with ceramide, cholesterol, a fatty acid, or the like. According to the present disclosure, cholesterol may be used in an amount of 5-15 wt %, particularly 5 wt % or more, 6 wt % or more, 7 wt % or more, 8 wt % or more, 9 wt % or more, 10 wt % or more, 11 wt % or more, 12 wt % or more, 13 wt % or more, or 14 wt % or more, and 15 wt % or less, 14 wt % or less, 13 wt % or less, 12 wt % or less, 11 wt % or less, 10 wt % or less, 9 wt % or less, 8 wt % or less, 7 wt % or less, or 6 wt % or less, and more particularly 11 wt % or 14 wt %, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester. However, the scope of the present disclosure is not limited thereto. In addition, according to an embodiment of the present disclosure, the weight ratio of ceramide to cholesterol may be 1:0.3-3, particularly 1:0.3 or more, 1:0.4 or more, 1:0.5 or more, 1:0.6 or more, 1:0.7 or more, 1:0.8 or more, 1:0.9 or more, 1:1 or more, 1:1.1 or more, 1:1.2 or more, 1:1.3 or more, 1:1.4 or more, 1:1.5 or more, 1:1.6 or more, 1:1.7 or more, 1:1.8 or more, 1:1.9 or more, 1:2 or more, 1:2.1 or more, 1:2.2 or more, 1:2.3 or more, 1:2.4 or more, 1:2.5 or more, 1:2.6 or more, 1:2.7 or more, 1:2.8 or more, or 1:2.9 or more, and 1:3 or less, 1:2.9 or less, 1:2.8 or less, 1:2.7 or less, 1:2.6 or less, 1:2.5 or less, 1:2.4 or less, 1:2.3 or less, 1:2.2 or less, 1:2.1 or less, 1:2 or less, 1:1.9 or less, 1:1.8 or less, 1:1.7 or less, 1:1.6 or less, 1:1.5 or less, 1:1.5 or less, 1:1.4 or less, 1:1.3 or less, 1:1.2 or less, 1:1.1 or less, 1:1 or less, 1:0.9 or less, 1:0.8 or less, 1:0.7 or less, 1:0.6 or less, 1:0.5 or less, or 1:0.4 or less, and more particularly 1:1 or 1:1.8. However, the scope of the present disclosure is not limited thereto.

According to the present disclosure, the unsaturated fatty acid is a $C_{10-30}$ unsaturated fatty acid having three or fewer double bonds and may be at least one selected from the group consisting of oleic acid, erucic acid, nervonic acid, linoleic acid and linolenic acid. Particularly, the unsaturated fatty acid may be oleic acid, erucic acid or nervonic acid, more particularly oleic acid, but is not limited thereto. The lipid composite composition according to the present disclosure may further include a saturated fatty acid, besides the unsaturated fatty acid, but is not limited thereto. According to the present disclosure, the $C_{10-30}$ unsaturated fatty acid having three or fewer double bonds may be used in an amount of 40-60 wt %, particularly 40 wt % or more, 42 wt % or more, 44 wt % or more, 46 wt % or more, 48 wt % or more, 50 wt % or more, 52 wt % or more 54 wt % or more, 55 wt % or more, 56 wt % or more, or 58 wt % or more, and 60 wt % or less, 58 wt % or less, 56 wt % or less, 55 wt % or less, 54 wt % or less, 52 wt % or less, 50 wt % or less, 48 wt % or less, 46 wt % or less, 44 wt % or less, or 42 wt % or less, more particularly 55 wt % or 58 wt %, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester. However, the scope of the present disclosure is not limited thereto. In addition, according to the present disclosure, the weight ratio of ceramide to the $C_{10-30}$ unsaturated fatty acid having three or fewer double bonds may be 1:2.5-12, particularly 1:2.5 or more, 1:3 or more, 1:3.5 or more, 1:4 or more, 1:4.5 or more, 1:5 or more, 1:5.5 or more, 1:6 or more, 1:6.5 or more, 1:7 or more, 1:7.5 or more, 1:8 or more, 1:8.5 or more, 1:9 or more, 1:9.2 or more, 1:9.5 or more, 1:10 or more, 1:10.5 or more, 1:11 or more, or 1:11.5 or more, and 1:12 or less, 1:11.5 or less, 1:11 or less, 1:10.5 or less, 1:10 or less, 1:9.5 or less, 1:9.2 or less, 1:9 or less, 1:8.5 or less, 1:8 or less, 1:7.5 or less, 1:7 or less, 1:6.5 or less, 1:6 or less, 1:5.5 or less, 1:5 or less, 1:4.5 or less, 1:4 or less, 1:3.5 or less, or 1:3 or less, more particularly 1:4.1 or 1:9.2. However, the scope of the present disclosure is not limited thereto.

The liquid lipid composite composition according to the present disclosure may include a $C_{10-60}$ fatty acid ester, or natural oil or wax containing a $C_{10-60}$ fatty acid ester. The fatty acid ester may be a $C_{10-60}$ fatty acid ester, particularly ethyl oleate, but is not limited thereto. The natural oil or wax containing a $C_{10-60}$ fatty acid ester may include a $C_{10-60}$ fatty acid ester as a main ingredient. The natural oil or wax may be at least one selected from the group consisting of jojoba oil, bees wax, carnauba wax and candelilla wax, particularly jojoba wax, but is not limited thereto. According to the present disclosure, the $C_{10-60}$ fatty acid ester, or natural oil or wax containing a $C_{10-60}$ fatty acid ester may be used in an amount of 5-30 wt %, particularly 5 wt % or more, 6 wt % or more, 8 wt % or more, 10 wt % or more, 12 wt % or more, 14 wt % or more, 16 wt % or more, 18 wt % or more, 20 wt % or more, 22 wt % or more, 24 wt % or more, 26 wt % or more, or 28 wt % or more, and 30 wt % or less, 28 wt % or less, 26 wt % or less, 24 wt % or less, 22 wt % or less, 20 wt % or less, 18 wt % or less, 16 wt % or less, 14 wt % or less, 12 wt % or less, 10 wt % or less, 8 wt % or less, or 6 wt % or less, and more particularly 14 wt % or 28 wt %, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester. However, the scope of the present disclosure is not limited thereto. In addition, according to the present disclosure, the weight ratio of ceramide to the $C_{10-60}$ fatty acid ester, or natural oil or wax containing a $C_{10-60}$ fatty acid ester may be 1:0.3-6, particularly 1:0.3 or more, 1:0.4 or more, 1:0.6 or more, 1:0.8 or more, 1:1 or more, 1:1.2 or more, 1:1.4 or more, 1:1.6 or more, 1:1.8 or more, 1:2 or more, 1:2.2 or more, 1:2.4 or more, 1:2.6 or more, 1:2.8 or more, 1:3 or more, 1:3.2 or more, 1:3.4 or more, 1:3.6 or more, 1:3.8 or more, 1:4 or more, 1:4.2 or more, 1:4.4 or more, 1:4.6 or more, 1:4.7 or more, 1:4.8 or more, 1:5 or more, 1:5.2 or more, 1:5.4 or more, 1:5.6 or more, or 1:5.8 or more, and 1:6 or less, 1:5.8 or less, 1:5.6 or less, 1:5.4 or less, 1:5.2 or less, 1:5 or less, 1:4.8 or less, 1:4.7 or less, 1:4.6 or less, 1:4.4 or less, 1:4.2 or less, 1:4 or less, 1:3.8 or less, 1:3.6 or less, 1:3.4 or less, 1:3.2 or less, 1:3 or less, 1:2.8 or less, 1:2.6 or less, 1:2.4 or less, 1:2.2 or less, 1:2 or less, 1:1.8 or less, 1:1.6 or less, 1:1.4 or less, 1:1.2 or less, 1:1 or less, 1:0.8 or less, 1:0.6 or less, or 1:0.4 or less, and more particularly 1:1 or 1:4.7. However, the scope of the present disclosure is not limited thereto.

The liquid lipid composite composition according to the present disclosure may include ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6, particularly 1:1:4.1:1 or 1:1.8:9.8:4.7, but is not limited thereto. According to an embodiment of the present disclosure, the lipid composite compositions (Comparative Examples 1-6, 8 and 9) including only two or three types of ingredients of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester, or the lipid composite composition (Comparative Example 7) including all of the four types of ingredients at a weight ratio of 1:1:1:17 cause precipitation during storage at room temperature, or during storage at room temperature after dilution with non-polar oil, and thus is not suitable for the formulation of a hair cosmetic composition. On the contrary, the lipid composite compositions (Examples 1-3) including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:1:4.1:1 or 1:1.8:9.8:4.7 are present in a liquid state at room temperature, and thus are shown to be easily applied to the formulation of a hair cosmetic composition (Test Examples 1 and 2).

The liquid lipid composite composition according to the present disclosure may include 5-15 wt % or ceramide, 5-15 wt % of cholesterol, 40-60 wt % of a $C_{10-30}$ unsaturated fatty acid having three or fewer double bonds, and 5-30 wt % of a $C_{10-60}$ fatty acid ester, or natural oil or wax containing a $C_{10-60}$ fatty acid ester, particularly 14 wt % or ceramide, 14 wt % of cholesterol, 58 wt % of a $C_{10-30}$ unsaturated fatty acid having three or fewer double bonds, and 14 wt % of a $C_{10-60}$ fatty acid ester, or natural oil or wax containing a $C_{10-60}$ fatty acid ester, or 6 wt % or ceramide, 11 wt % of cholesterol, 55 wt % of a $C_{10-30}$ unsaturated fatty acid having three or fewer double bonds, and 28 wt % of a $C_{10-60}$ fatty acid ester, or natural oil or wax containing a $C_{10-60}$ fatty acid ester, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester. However, the scope of the present disclosure is not limited thereto. According to an embodiment of the present disclosure, the lipid composite compositions (Comparative Examples 1-6, 8 and 9) including only two or three types of ingredients of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester, or the lipid composite composition (Comparative Example 7) including all of the four types of ingredients in an amount of 5 wt %, 5 wt %, 5 wt % and 85 wt %, respectively, cause precipitation during storage at room temperature, or during storage at room temperature after dilution with non-polar oil, and thus is not suitable for the formulation of a hair cosmetic composition. On the contrary, the lipid composite compositions (Examples 1 and 3) including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester in an amount of 14 wt %, 14 wt %, 58 wt % and 14 wt %, respectively, and the lipid composite composition (Example 2) including all of the four types of ingredients in an amount of 6 wt %, 11 wt %, 55 wt % and 28 wt %, respectively, are present in a liquid state at room temperature, and thus are shown to be easily applied to the formulation of a hair cosmetic composition (Test Examples 1 and 2).

The liquid lipid composite composition according to the present disclosure can be present in a liquid state at room temperature by including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6. The liquid sate may be an oil phase or aqueous phase, particularly oil phase. The lipid composite composition according to the present disclosure is a liquid lipid composite composition present in a liquid state at room temperature, and thus can be easily applied to the formulation of a hair cosmetic composition.

The liquid lipid composite composition according to the present disclosure is a lipid composite composition including lipid ingredients present in hair, i.e. ceramide, cholesterol, an unsaturated fatty acid and a fatty acid ester, and thus simulating lipids present in hair. Therefore, when lipids are reduced in hair damaged by various causes, the liquid lipid composite composition is useful for improving such a damaged hair condition, if the hair is treated with the liquid lipid composite composition.

The liquid lipid composite composition which includes ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 may be used for improving a hair condition. Herein, the expression 'improving a hair condition' may refer to restoring hair damaged by physical or chemical stimuli nearly into its original state, particularly may refer to increasing hair elasticity and strength, increasing hair shininess or enhancing hair softness, but is not limited thereto.

Particularly, the expression 'enhancing hair softness' may refer to a decrease in frictional force of hair of 50% or more, particularly 52% or more, 54% or more, 56% or more, 58% or more, or 60% or more, and more particularly 58% or more, before and after treating hair with the lipid composite composition. According to an embodiment of the present disclosure, the lipid composite compositions (Comparative Examples 1-6, 8 and 9) including only two or three types of ingredients of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester, or the lipid composite composition (Comparative Example 7) including all of the four types of ingredients at a weight ratio of 1:1:1:17 show a decrease in frictional force of 18-48%, before and after treating hair with each composition. On the contrary, the compositions (Examples 1 and 3) including all of the four ingredients at a weight ratio of 1:1:4.1:1 show a decrease in frictional force of 58% or 60%, and the composition (Example 2) including all of the four ingredients at a weight ratio of 1:1.8:9.8:4.7 shows a decrease in frictional force of 60%. Thus, treatment with the lipid composite composition according to the present disclosure provides a larger decrease in frictional force. Thus, it is shown that when hair is treated with the lipid composite composition according to the present disclosure, softness of damaged hair is enhanced significantly, thereby providing an excellent effect of improving a hair condition (Test Example 3).

In addition, 'increasing hair shininess' may refer to an increase in hair shininess of 55% or more, particularly 55% or more, 56% or more, 57% or more, 58% or more, 59% or more, 60% or more, 61% or more, 62% or more, or 63% or more, before and after treating hair with the lipid composite composition. According to an embodiment of the present disclosure, the lipid composite compositions (Comparative Examples 2-6, 8 and 9) including only two or three types of ingredients of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester, or the lipid composite composition (Comparative Example 7) including all of the four types of ingredients at a weight ratio of 1:1:1:17 show an increase in hair shininess of 12-51%, before and after treating hair with each composition. On the contrary, the composition (Example 1) including all of the four ingredients at a weight ratio of 1:1:4.1:1 shows an increase in shininess of 62% and the composition (Example 2) including all of the four ingredients at a weight ratio of 1:1.8:9.8:4.7 shows an increase in shininess of 63%. Thus, treatment with the lipid composite composition according to the present disclosure provides a larger increase in shininess. Thus, it is shown that when hair is treated with the lipid composite composition according to the present disclosure, shininess of damaged hair is increased significantly, thereby providing an excellent effect of improving a hair condition (Test Example 4).

In this context, the liquid lipid composite composition may be a cosmetic composition, particularly a hair cosmetic composition.

The hair cosmetic composition may have a conventional formulation. For example, it may be formulated into shampoo, hair treatment, hair lotion, hair serum, hair essence, or the like. Each formulation of the hair cosmetic composition may include various ingredients used for a conventional hair cosmetic composition depending on the particular formulation or final purpose, and types and contents of such ingredients may be selected with ease by those skilled in the art.

In addition, the cosmetic composition according to the present disclosure may include the liquid lipid composite composition according to the present disclosure in an amount of 0.01-50 wt % based on the total weight of the cosmetic composition. Particularly, the cosmetic composition may include the liquid lipid composite composition in an amount of 0.1-20 wt % in order to stabilize its formulation.

To the hair shampoo composition including the liquid lipid composite composition according to the present disclosure, ingredients suitable for the particular type of the composition may be added. For example, in the shampoo composition including a synthetic surfactant as a conventional detergent ingredient, preservative, thickener and viscosity modifier, pH modifier, fragrance, dye, hair conditioning agent and water, the synthetic surfactant may be any one selected from anionic, amphoteric and non-ionic surfactants. The synthetic surfactant may be used in an amount of 10-70 wt %, particularly 10-30 wt %, based on the total weight of the cosmetic composition. The synthetic anionic surfactant may be an alkyl and alkyl ether sulfate, and particular examples thereof include sodium lauryl sulfate, ammonium lauryl sulfate, triethanolamine lauryl sulfate, polyoxyethylene sodium lauryl sulfate, polyoxyethylene ammonium lauryl sulfate, or the like. The synthetic amphoteric surfactant may be an alkyl betaine and alkylamidopropyl betaine, and particular examples thereof include cocodimethyl carboxymethyl betaine, lauryldimethyl carboxymethyl betaine, lauryldimethyl alpha-carboxyethyl betaine, cetyldimethyl carboxymethyl betaine, cocoamidopropyl betaine, or the like. The synthetic non-ionic surfactant may be an alkanolamide and amine oxide, and particular examples thereof include lauryl diethyl amine oxide, coconut oil alkyl dimethyl amine oxide, lauric acid diethanolamide, coconut oil fatty acid diethanolamide, coconut oil fatty acid monoethanolamide, or the like. The above-mentioned surfactants may be selected and used alone or in combination in the hair cosmetic composition including the liquid lipid composite composition according to the present disclosure.

The hair cosmetic composition according to the present disclosure may further include currently used optional ingredients for maintaining basic physical properties and quality, and such optional ingredients are known to those skilled in the art. The optional ingredients include a pearlizing agent, preservative, viscosity modifier, pH modifier, fragrance, dye, hair conditioning agent, or the like. Particular examples of the pearlizing agent include glycol distearate, glycol monostearate, fatty acid, or the like. Particular examples of the preservative include sodium benzoate, phenoxyethanol, or the like, and such preservatives may be used alone or in combination. Particular examples of the viscosity modifier include amide-based non-ionic surfactants, such as cocoamide MEA (CME), cocoamide DEA (CDE), sodium chloride, or the like. Particular examples of the pH modifier include sodium phosphate, disodium phosphate, citric acid, sodium citrate, or the like. Particular examples of the hair conditioning agent include dimethicone bases, cationic polymers, or the like, and such hair conditioning agents may be used alone or in combination in an amount of 0.1-10 wt %, particularly 0.5-5 wt %, based on the total weight of the cosmetic composition.

The hair treatment composition including the liquid lipid composite composition according to the present disclosure may further include suitable ingredients depending on the particular type of the composition. For example, the composition may include conventional treatment ingredients, such as cationic surfactants including tertiary amidoamines and quaternary ammonium compounds, high-melting point compounds, silicon compounds, and optional ingredients, such as a preservative, thickener, viscosity modifier, pH modifier, fragrance, or the like. The quaternary ammonium compounds as cationic surfactants in the hair treatment composition include alkyl (14-22) trimethylammonium chlorides, dialkyl (14-22) dimethyl ammonium chlorides, hydrogenated tallow alkyl trimethyl ammonium chlorides, ditallow alkyl dimethyl ammonium chlorides, or the like. In addition, particular examples of the tertiary amidoamines include cocoamidopropyl dimethyl amine, stearamidopropyl dimethyl amine, behenylamidopropyl dimethyl amine, oleamidopropyl dimethyl amine, isostearamidopropyl dimethyl amine, or the like. Further, the amine compounds may be used after being neutralized with an acid, such as L-glutamic acid, lactic acid, hydrochloric acid, malic acid, succinic acid, acetic acid, fumaric acid, citric acid, EDTA, or the like. Such cationic surfactants may be used alone or in combination in an amount of 0.1-30 wt %, particularly 0.5-10 wt %, based on the total weight of the cosmetic composition. The high-melting point compound may be a fatty alcohol-based compound, fatty acid-based compound, fatty alcohol derivative, hydrocarbon-based compound or a mixture thereof, and particular examples thereof include cetyl alcohol, stearyl alcohol, cetostearyl alcohol, or the like. The high-melting point compound may be used in an amount of 0.1-20 wt % based on the total weight of the treatment composition. Particular examples of the silicon compound may include polyalkylsiloxane-based, polyarylsiloxane-based, polyalkylarylsiloxane-based, polyethersiloxane copolymers and mixtures thereof, cyclopolysiloxane and suitable alkylamino-substituted compounds, amodimethicone, or the like.

According to the present disclosure, optional ingredients may be used for maintaining basic physical properties and quality, and such optional ingredients are known to those skilled in the art. Particular examples of such optional ingredients include a preservative, pH modifier, fragrance, or the like.

In another aspect of the present disclosure, there is provided a method for improving a hair condition, including administrating a liquid lipid composite composition, which includes ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6, to a subject in need of improvement of a hair condition, or treating the subject with the liquid lipid composite composition. According to an embodiment of the present disclosure, the administration or treatment may be carried out by the administration or treatment method or with the administration or treatment dose disclosed herein.

In still another aspect of the present disclosure, there is provided use of a combination of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 for the preparation of a cosmetic composition for improving a hair condition.

In still another aspect of the present disclosure, there is provided use of a liquid lipid composite composition, which includes ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6, for improving a hair condition.

In yet another aspect of the present disclosure, there is provided a liquid lipid composite composition, which includes ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6, for use in improvement of a hair condition.

Exemplary embodiments now will be described more fully hereinafter. The present disclosure may, however, be embodied in many different forms and should not be construed as limited to the exemplary embodiments set forth therein.

[Preparation Example] Preparation of Lipid Composite Compositions

According to the following Table 1 and Table 2, each of the ingredients was weighed in a predetermined amount, dissolved under warming and cooled to room temperature to obtain the lipid composite compositions of Comparative Examples 1-9 and Examples 1-3. In Table 1 and Table 2, PC-104 is pseudoceramide represented by the following Chemical Formula 2. In addition, the content of each ingredient in Table 1 and Table 2 is expressed by wt % based on the total weight of the ingredients contained in each composition.

[Chemical Formula 2]

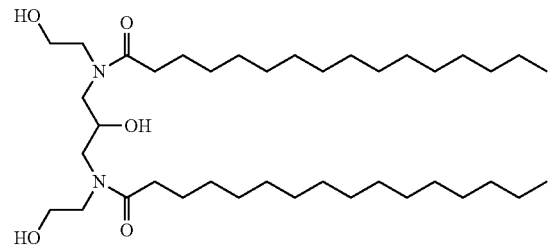

TABLE 1

Ingredients of Lipid Composite Compositions and Content of Each Ingredient (unit: wt %)

| Ingredients | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|
| PC-104 | 5 | — | 5 | — | 5 | 5 | 5 | 17 | 17 |
| Oleic acid | 95 | 95 | — | — | — | — | 5 | 66 | 66 |
| Stearic acid | — | — | — | — | 90 | 5 | — | — | — |
| Cholesterol | — | 5 | — | 5 | 5 | 5 | 5 | — | 17 |
| Jojoba oil | — | — | 95 | 95 | — | 85 | 85 | 17 | — |
| Ethyl oleate | — | — | — | — | — | — | — | — | — |
| Total | 100 | 100 | 100 | 100 | 100 | 100 | 100 | 100 | 100 |

TABLE 2

Ingredients of Lipid Composite Compositions and Content of Each Ingredient (unit: wt %)

| Ingredients | Example 1 | Example 2 | Example 3 |
|---|---|---|---|
| PC-104 | 14 | 6 | 14 |
| Oleic acid | 58 | 55 | 58 |
| Stearic acid | — | — | — |
| Cholesterol | 14 | 11 | 14 |
| Jojoba oil | 14 | 28 | — |
| Ethyl oleate | — | — | 14 |
| Total | 100 | 100 | 100 |

[Test Example 1] Observation of Precipitation during Storage at Room Temperature While each of the lipid composite compositions (Comparative Examples 1-9 and Examples 1-3) according to Preparation Example was stored at room temperature for 3 days, it was observed whether precipitation or solidification occurred in each composition or not. The results are shown in the following Table 3.

TABLE 3

Precipitation during Storage at Room Temperature

| | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Ex. 1 | Ex. 2 | Ex. 3 |
|---|---|---|---|---|---|---|---|---|---|---|---|---|
| Precipitation | ○ | ○ | ○ | ○ | ○ | ○ | ○ | ○ | X | X | X | X |

As shown in Table 3, each of the compositions (Comparative Examples 1-4 and 8) including only two or three types of ingredients selected from PC-104 as pseudoceramide, cholesterol, oleic acid as an unsaturated fatty acid and jojoba oil as natural oil, and the compositions (Comparative Examples 5 and 6) including stearic acid as a saturated fatty acid, instead of an unsaturated fatty acid, causes precipitation during storage at room temperature. In addition, the composition including PC-104, cholesterol, oleic acid and jojoba oil at a weight ratio of 1:1:1:17 according to Comparative Example 7 causes precipitation during storage at room temperature. On the contrary, each of the compositions (Examples 1-3) including PC-104, cholesterol, oleic acid and jojoba oil or ethyl oleate at a weight ratio of 1:1:4.1:1 or 1:1.8:9.2:4.7 causes no precipitation during storage at room temperature. It can be seen from the above results that the lipid composite composition including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 according to the present disclosure contains a high content of ceramide and is present in a liquid state during storage at room temperature, and thus can be easily formulated as a hair cosmetic composition.

[Test Example 2] Observation of Precipitation upon Dilution with Non-Polar Oil

While each of the lipid composite compositions (Comparative Examples 1-9 and Examples 1-3) according to Preparation Example was diluted with isododecane as non-polar oil to 5% and stored at room temperature for 3 days, it was observed whether precipitation or solidification occurred in each composition or not. The results are shown in the following Table 4.

TABLE 4

Precipitation upon Dilution with Non-Polar Oil

| | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Ex. 1 | Ex. 2 | Ex. 3 |
|---|---|---|---|---|---|---|---|---|---|---|---|---|
| Precipitation | ◯ | ◯ | ◯ | ◯ | ◯ | ◯ | ◯ | ◯ | ◯ | X | X | X |

As shown in Table 4, each of the compositions (Comparative Examples 1-4, 8 and 9) including only two or three types of ingredients selected from PC-104, cholesterol, oleic acid and jojoba oil as natural oil, and the compositions (Comparative Examples 5 and 6) including stearic acid as a saturated fatty acid, instead of an unsaturated fatty acid, causes precipitation upon dilution with isododecane. In addition, the composition including PC-104, cholesterol, oleic acid and jojoba oil at a weight ratio of 1:1:1:17 according to Comparative Example 7 causes precipitation upon dilution with isododecane. On the contrary, it is shown that each of the compositions (Examples 1-3) including PC-104, cholesterol, oleic acid and jojoba oil or ethyl oleate at a weight ratio of 1:1:4.1:1 or 1:1.8:9.2:4.7 significantly improves the problem of precipitation during storage at room temperature after dilution with isododecane. It can be seen from the above results that the lipid composite composition including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 according to the present disclosure contains a high content of ceramide and is present in a liquid state upon dilution with non-polar oil added for the formulation of a cosmetic composition, particularly a hair cosmetic composition, and thus can be easily formulated as a hair cosmetic composition.

[Test Example 3] Determination of Hair Frictional Force

Damaged hair tress was prepared by using a decolorizing agent, and the frictional force before the treatment with a lipid composite composition was determined by using MTT (Miniature Tensile Tester) 175 instrument. Then, the damaged hair tress was treated with 120 μL of a sample, prepared by diluting each of the lipid composite compositions (Comparative Examples 1-9 and Examples 1-3) according to Preparation Example with isododecane to 10%, by applying the sample uniformly to the damaged hair tress, and the frictional force after the treatment with the lipid composite composition was determined by using MTT (Miniature Tensile Tester) 175 instrument. The result of a decrease in frictional force for each sample are shown in the following Table 5.

In Table 5, a decrease in frictional force was calculated according to the following formula.

Decrease in frictional force (%)=(Frictional force before treating hair with a composition−Frictional force after treating hair with a composition)/(Frictional force before treating hair with a composition)×100

TABLE 5

Decrease in Frictional Force (unit: %)

| | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Ex. 1 | Ex. 2 | Ex. 3 |
|---|---|---|---|---|---|---|---|---|---|---|---|---|
| Decrease in frictional force | 32 | 28 | 26 | 18 | 23 | 40 | 32 | 41 | 48 | 58 | 60 | 60 |

As shown in Table 5, each of the compositions (Comparative Examples 1-4, 8 and 9) including only two or three types of ingredients selected from PC-104, cholesterol, oleic acid and jojoba oil as natural oil, the compositions (Comparative Examples 5 and 6) including stearic acid as a saturated fatty acid, instead of an unsaturated fatty acid, and the composition (Comparative Example 7) including PC-104, cholesterol, oleic acid and jojoba oil at a weight ratio of 1:1:1:17 show a decrease in frictional force of 18-48%. On the contrary, it is shown that each of the compositions (Examples 1-3) including PC-104, cholesterol, oleic acid and jojoba oil or ethyl oleate at a weight ratio of 1:1:4.1:1 or 1:1.8:9.2:4.7 according to the present disclosure shows a decrease in frictional force of 58-60%. Thus, it can be seen that treatment with the lipid composite composition according to the present disclosure provides a larger decrease in frictional force. As a result, it can be seen from the above results that when damaged hair is treated with the lipid composite composition including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 according to the present disclosure, it is possible to enhance the softness of damaged hair more significantly.

[Test Example 4] Determination of Hair Shininess

Hair tress was prepared, and the shininess before the treatment with a lipid composite composition was determined by using SAMBA hair system instrument. Then, the hair tress was treated with 120 μL of a sample, prepared by diluting each of the lipid composite compositions (Comparative Examples 2-9 and Examples 1 and 2) according to Preparation Example with isododecane to 10%, by applying the sample uniformly to the hair tress, and the shininess after the treatment with the lipid composite composition was determined by using SAMBA hair system instrument. The result of an increase in shininess for each sample are shown in the following Table 6.

In Table 6, an increase in shininess was calculated according to the following formula.

Increase in shininess (%)=(Shininess before treating hair with a composition−Shininess after treating hair with a composition)/(Shininess before treating hair with a composition)×100

TABLE 6

Increase in Shininess (unit: %)

| | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Ex. 1 | Ex. 2 |
|---|---|---|---|---|---|---|---|---|---|---|
| Increase in shininess | 51 | 30 | 23 | 12 | 32 | 32 | 47 | 43 | 62 | 63 |

As shown in Table 6, each of the compositions (Comparative Examples 2-4, 8 and 9) including only two or three types of ingredients selected from PC-104, cholesterol, oleic acid and jojoba oil as natural oil, the compositions (Comparative Examples 5 and 6) including stearic acid as a saturated fatty acid, instead of an unsaturated fatty acid, and the composition (Comparative Example 7) including PC-104, cholesterol, oleic acid and jojoba oil at a weight ratio of 1:1:1:17 show an increase in shininess of 12-51%. On the contrary, it is shown that each of the compositions (Examples 1 and 2) including PC-104, cholesterol, oleic acid and jojoba oil or ethyl oleate at a weight ratio of 1:1:4.1:1 or 1:1.8:9.2:4.7 according to the present disclosure shows an increase in shininess of 62-63%. Thus, it can be seen that treatment with the lipid composite composition according to the present disclosure provides a larger increase in shininess. As a result, it can be seen from the above results that when damaged hair is treated with the lipid composite composition including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 according to the present disclosure, it is possible to increase the shininess of damaged hair more significantly.

It can be seen from the foregoing that the lipid composite composition including ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester at a weight ratio of 1:0.3-3:2.5-12:0.3-6 contains a high content of ceramide, is present in a liquid state during storage at room temperature regardless of dilution with non-polar oil, and thus can be easily formulated as a hair cosmetic composition. This demonstrates that when hair is treated with the liquid lipid composite composition according to the present disclosure, it is possible to obtain excellent effects of improving a hair condition, including enhancing hair softness, increasing hair elasticity and strength, increasing hair shininess, or the like.

Hereinafter, formulation examples of the composition according to the present disclosure will be explained. However, the following examples are for illustrative purposes only and the scope of the present disclosure is not limited thereto.

[Formulation Example 1] Hair Tonic

Hair tonic was prepared according to the composition as shown in the following Table 7 by using the conventional method.

TABLE 7

| Ingredients | Content (wt %) |
|---|---|
| Ethanol | 50.0 |
| Menthol | 0.02 |
| Glycerin | 3.0 |
| Salicylic acid | 0.05 |

TABLE 7-continued

| Ingredients | Content (wt %) |
|---|---|
| Liquid lipid composite composition according to Example 1 | 2.0 |
| Fragrance and pigment | q.s. |
| Purified water | Balance (to 100) |

[Formulation Example 2] Hair Lotion

Hair lotion was prepared according to the composition as shown in the following Table 8 by using the conventional method.

TABLE 8

| Ingredients | Content (wt %) |
|---|---|
| Cetostearyl alcohol | 2.0 |
| EDTA 2Na | 0.2 |
| Hydroxyethyl cellulose | 0.5 |
| Mineral oil | 5.0 |
| Liquid lipid composite composition according to Example 1 | 2.0 |
| Preservative | q.s. |
| Fragrance and pigment | q.s. |
| Purified water | Balance (to 100) |

[Formulation Example 3] Hair Nutrient Skin

Hair nutrient skin was prepared according to the composition as shown in the following Table 9 by using the conventional method.

TABLE 9

| Ingredients | Content (wt %) |
|---|---|
| Bees wax | 4.0 |
| Polysorbate 60 | 1.5 |
| Sorbitan sesquioleate | 0.7 |
| Mineral oil | 10.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Liquid lipid composite composition according to Example 1 | 2.0 |
| Preservative | q.s. |

TABLE 9-continued

| Ingredients | Content (wt %) |
| --- | --- |
| Fragrance and pigment | q.s. |
| Purified water | Balance (to 100) |

[Formulation Example 4] Hair Shampoo

Hair shampoo was prepared according to the composition as shown in the following Table 10 by using the conventional method.

TABLE 10

| Ingredients | Content (wt %) |
| --- | --- |
| Purified water | Balance (to 100) |
| Liquid lipid composite composition according to Example 1 | 2.0 |
| Sodium lauryl sulfate | 36.0 |
| Cocoamidopropyl betaine | 8.0 |
| Palmitidine maleate | 2.0 |
| Glycol stearate | 1.5 |
| Polyquaternium 10 | 0.5 |
| Citric acid | 0.1 |
| Glycerin | 2.0 |
| Preservative, pigment and fragrance | q.s. |

[Formulation Example 5] Hair Rinse or Treatment

Hair rinse or treatment was prepared according to the composition as shown in the following Table 11 by using the conventional method.

TABLE 11

| Ingredients | Content (wt %) |
| --- | --- |
| Purified water | Balance (to 100) |
| Liquid lipid composite composition according to Example 1 | 2.0 |
| Propylene glycol | 2.0 |
| Cetyltrimethylammonium chloride | 1.0 |
| Cetyl alcohol | 3.0 |
| Stearyl alcohol | 3.0 |
| Mineral oil | 0.5 |
| Citric acid | 0.2 |
| Polydimethyl siloxane | 1.0 |
| Preservative, pigment and fragrance | q.s. |

The invention claimed is:

1. A liquid lipid composite composition which comprises ceramide, cholesterol, a $C_{10-30}$ fatty acid, and a $C_{10-60}$ fatty acid ester, or natural oil or wax containing a $C_{10-60}$ fatty acid ester at a weight ratio of 1:0.3-3:12.5-12:0.3-6, wherein the ceramide is pseudoceramide wherein the $C_{10-30}$ fatty acid is $C_{10-30}$ unsaturated fatty acid having three or fewer double bonds.

2. The liquid lipid composite composition according to claim 1, wherein the pseudoceramide is a compound represented by the following Chemical Formula 1:

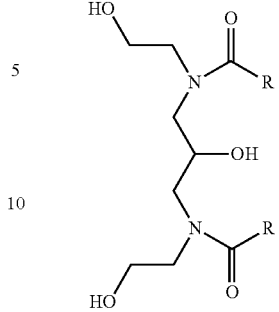

[Chemical Formula 1]

wherein R is a $C_{2-25}$ alkyl.

3. The liquid lipid composite composition according to claim 2, wherein R is $C_{15}H_{31}$.

4. The liquid lipid composite composition according to claim 1, wherein the $C_{10-30}$ unsaturated fatty acid having three or fewer double bonds is at least one selected from the group consisting of oleic acid, erucic acid, nervonic acid, linoleic acid and linolenic acid.

5. The liquid lipid composite composition according to claim 1, wherein the $C_{10-60}$ fatty acid ester is ethyl oleate.

6. The liquid lipid composite composition according to claim 1, wherein the natural oil or wax containing a $C_{10-60}$ fatty acid ester is at least one selected from the group consisting of jojoba oil, bees wax, carnauba wax and candelilla wax.

7. The liquid lipid composite composition according to claim 1, which comprises 5-15 wt % of ceramide, 5-15 wt % of cholesterol, 40-60 wt % of a $C_{10-30}$ unsaturated fatty acid having three or fewer double bonds, and 5-30 wt % of a $C_{10-60}$ fatty acid ester, or natural oil or wax containing a $C_{10-60}$ fatty acid ester, based on the total weight of ceramide, cholesterol, a $C_{10-30}$ unsaturated fatty acid having three or fewer double bonds, and a $C_{10-60}$ fatty acid ester, or natural oil or wax containing a $C_{10-60}$ fatty acid ester.

8. The liquid lipid composite composition according to claim 1, which is present in a liquid state at room temperature.

9. A method for improving a hair condition comprising administering an effective amount of the composition according to claim 1 to a subject in need thereof.

10. The method according to claim 9, wherein the improving a hair condition is an increase in hair elasticity and strength, an increase in hair shininess, or enhancement of hair softness.

11. The liquid lipid composite composition according to claim 1, which is a cosmetic composition.

12. A method for improving a hair condition comprising administering an effective amount of the composition according to claim 1 to a subject in need thereof.

13. A method for improving a hair condition comprising administering an effective amount of the composition according to claim 2 to a subject in need thereof.

14. A method for improving a hair condition comprising administering an effective amount of the composition according to claim 3 to a subject in need thereof.

15. A method for improving a hair condition comprising administering an effective amount of the composition according to claim 4 to a subject in need thereof.

16. A method for improving a hair condition comprising administering an effective amount of the composition according to claim 5 to a subject in need thereof.

17. A method for improving a hair condition comprising administering an effective amount of the composition according to claim 6 to a subject in need thereof.

18. A method for improving a hair condition comprising administering an effective amount of the composition according to claim 7 to a subject in need thereof.

19. A method for improving a hair condition comprising administering an effective amount of the composition according to claim 8 to a subject in need thereof.

\* \* \* \* \*